(12) United States Patent
Jones

(10) Patent No.: US 10,085,876 B2
(45) Date of Patent: Oct. 2, 2018

(54) FEMALE URINATION DEVICE

(71) Applicant: David Arthur Jones, Warsaw (PL)

(72) Inventor: David Arthur Jones, Warsaw (PL)

(*) Notice: Subject to any disclaimer, the term of this patent is extended or adjusted under 35 U.S.C. 154(b) by 381 days.

(21) Appl. No.: 14/882,175

(22) Filed: Oct. 13, 2015

(65) Prior Publication Data
US 2016/0030228 A1 Feb. 4, 2016

Related U.S. Application Data

(63) Continuation-in-part of application No. 29/476,751, filed on Dec. 17, 2013, now Pat. No. Des. 747,469.

(51) Int. Cl.
*A61F 5/44* (2006.01)
*A61F 5/455* (2006.01)

(52) U.S. Cl.
CPC .............. *A61F 5/4556* (2013.01); *A61F 5/44* (2013.01); *A61F 5/455* (2013.01)

(58) Field of Classification Search
CPC ........... A61F 5/4556; A61F 5/44; A61F 5/455
See application file for complete search history.

(56) References Cited

U.S. PATENT DOCUMENTS

| 3,964,111 | A | * | 6/1976 | Packer | A61F 5/4556 4/144.4 |
| 4,202,058 | A | * | 5/1980 | Anderson | A61F 5/455 4/144.3 |
| 4,528,703 | A | * | 7/1985 | Kraus | A61F 5/4556 4/144.1 |
| 8,597,207 | B1 | * | 12/2013 | Perry | A61F 5/455 600/574 |
| 2003/0195483 | A1 | * | 10/2003 | Ching | A61F 5/4556 604/327 |
| 2007/0006368 | A1 | * | 1/2007 | Key | A61B 10/007 4/144.2 |
| 2007/0191795 | A1 | * | 8/2007 | Di Croce | A61F 5/4556 604/347 |
| 2009/0216206 | A1 | * | 8/2009 | Nishtala | A61M 39/10 604/327 |

* cited by examiner

*Primary Examiner* — Ariana Zimbouski

(57) ABSTRACT

A female urination device that allows a woman to urinate while standing includes a fluid collecting body and a sanitary napkin. The fluid collecting body has a concave interior surface and a convex exterior surface that are positioned in between a spout and a rim. The concave interior surface delineates a fluid collecting portion, while the rim delineates a vulval opening. The spout is in fluid communication with the vulval opening through the fluid collecting portion, wherein urine is able to freely pass through the fluid collecting body. The concave interior surface and the convex exterior surface are tapered from the rim to the spout, while the spout is tapered away from the concave interior surface and the convex exterior surface to facilitate the control of the flow of urine. The sanitary napkin is positioned around the rim and assists in adhering the fluid collecting body to the woman's body.

20 Claims, 10 Drawing Sheets

FEMALE URINATION DEVICE

The current application is a continuation in part of U.S. Design patent application Ser. No. 29/476,751 filed on Dec. 17, 2013.

FIELD OF THE INVENTION

The present invention relates generally to a female urination device (FUD), otherwise known as a stand-to-pee (STP) device. More specifically, the present invention is a portable device that allows a woman to urinate standing up, while directing the flow of urine away from the woman's body and clothing.

BACKGROUND OF THE INVENTION

A natural problem encountered by women is the need to urinate in a normal, toilet sitting position in situations that are unsanitary, uncomfortable, or simply inconvenient. Public restrooms are used by innumerable people on a daily basis and as can be imagined, become breeding grounds for pathogens such as bacteria, viruses, and fungi. Poor maintenance of these restroom facilities results in unsightly, grimy, and foul conditions. Several products are available to allow women to circumvent the conventional toilet sitting position while urinating. These products are primarily intended for women who wish to avoid using unsanitary public restrooms as well as women who do not have direct access to restrooms, for example in the outdoors. Female urination devices (FUDs), also known as stand-to-pee (STP) devices, generally encompass devices featuring an open entryway connected to a cone shaped funnel or elongated nozzle to direct the flow of urine away from the user's body, sometimes into a bottle.

The funnels and nozzles commonly found on many devices contribute to an overall increase in size and weight of the devices while hindering their collapsibility and portability. Another common deficiency found in the prior art is the lack of a properly conformed seal between a device and the user's body. This often results in leakage onto the user's hands and/or clothes as urine enters into the device. An additional problem exhibited by some devices encompasses non-hypoallergenic materials of which the devices are composed. These devices may cause allergic reactions on a user's skin. The present invention seeks to address the issues raised by the existing prior art and improve upon the prior art as well.

The present invention is a female urination device that allows women to urinate in a standing position while directing the flow of urine away from their bodies. In the preferred embodiment, the present invention comprises a fluid collecting body with a concave interior surface and a convex exterior surface. The fluid collecting body has a vulval opening that is delineated by a rim that is shaped to receive the bilateral symmetry of a female human crotch. The concave interior surface delineates a fluid collecting portion that is positioned above a spout, wherein the spout is directed towards the front end of the fluid collecting body. During urination, urine is able to enter the fluid collecting portion of the fluid collecting body through the vulval opening before traveling downward by the force of gravity and exiting through the spout. The material of the present invention is flexible in order to allow the user to firmly press the device against her body to prevent leakage.

The object of the present invention is to allow a woman to urinate in a standing position. To use the present invention, a woman positions the fluid collecting body such that the spout is aligned with her labia majora and urinates into the interior of the fluid collecting body. The concave interior surface prevents the spraying urine from exiting the fluid collecting body during use, except through the spout. Urine enters the fluid collecting portion and exits the fluid collecting body through the spout and away from the user. The present invention seeks to direct the flow of urine away from the user by making the fluid arc without the need for an elongated nozzle. Additionally, the present invention capitalizes on the force of gravity as urine is directed into the fluid collecting portion and forced out of the spout. The present invention is collapsible for improved portability due to the flexible material of the device. Furthermore, the present invention is available in both disposable and reusable variants.

DETAIL DESCRIPTIONS OF THE INVENTION

All illustrations of the drawings are for the purpose of describing selected versions of the present invention and are not intended to limit the scope of the present invention.

The present invention is a female urination device for directing the flow of urine away from a user's body. The present invention comprises a fluid collecting body 10 that is used to collect and direct urine away from the user's body and a sanitary napkin 80 that is used to facilitate application of the present invention to the user's body. In addition to being used to control the flow of urine, the present invention provides an external device that can be used to control a woman's menstrual outflow.

Figure 1:
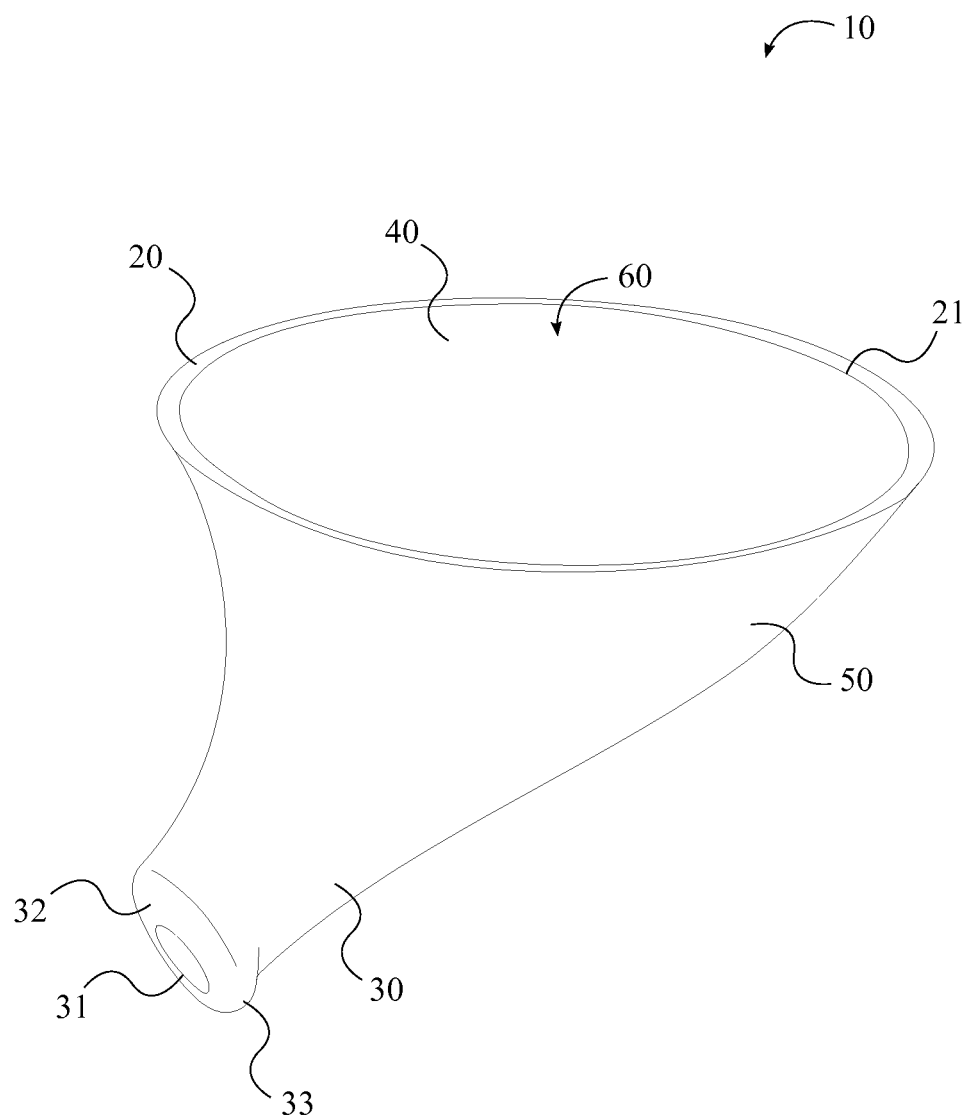
FIG. 1 is a perspective view of the present invention.

In reference to FIG. 1, the fluid collecting body 10 comprises a rim 20, a spout 30, a concave interior surface 40, and a convex exterior surface 50. In the preferred embodiment of the present invention, the fluid collecting body 10 is a one-piece device composed of a flexible, hypoallergenic material. The material is flexible to assist in conforming to a user's body to prevent leakage during use, and the material can be easily cleaned with soap and water after every use. Furthermore, the flexibility of the material increases collapsibility and portability of the fluid collecting body 10 when not in use as well. In other embodiments of the present invention, the fluid collecting body 10 is disposable and as such the material of the fluid collecting body 10 is biodegradable to be environmentally friendly upon being discarded.

In further reference to FIG. 1, the fluid collecting body 10 is a thin walled structure, wherein the concave interior surface 40 delineates a fluid collecting portion 60 being the hollow interior of the fluid collecting body 10. The convex exterior surface 50 assists the user in holding the device to the user's body. The concave interior surface 40 and the convex exterior surface 50 are positioned in between the spout 30 and the rim 20, wherein the spout 30 is perimetrically connected to both the concave interior surface 40 and the convex exterior surface 50. Additionally, the concave interior surface 40 and the convex exterior surface 50 are tapered from the rim 20 to the spout 30. The curved and tapered nature of the concave interior surface 40 facilitates the flow of urine, or menstrual outflow, towards the spout 30.

Figure 2:
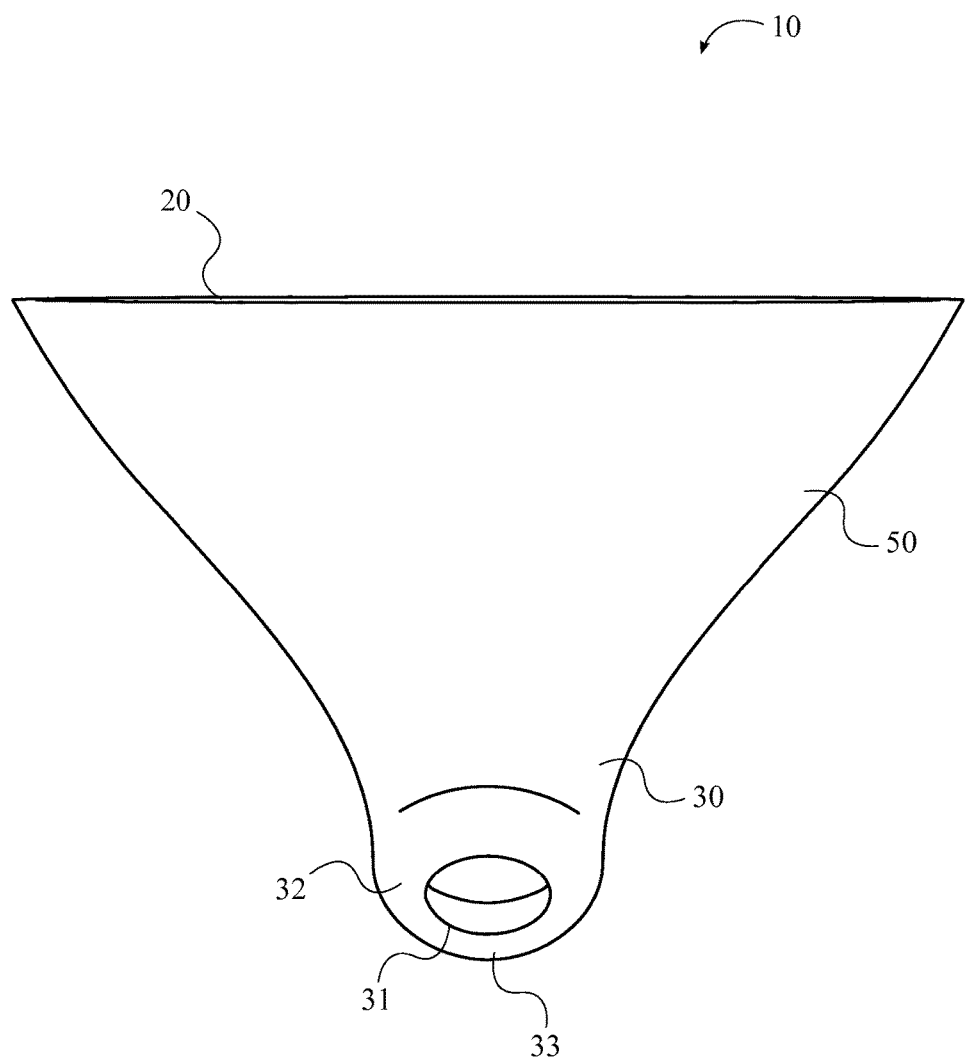
FIG. 2 is a front elevational view of the present invention.
Figure 3:
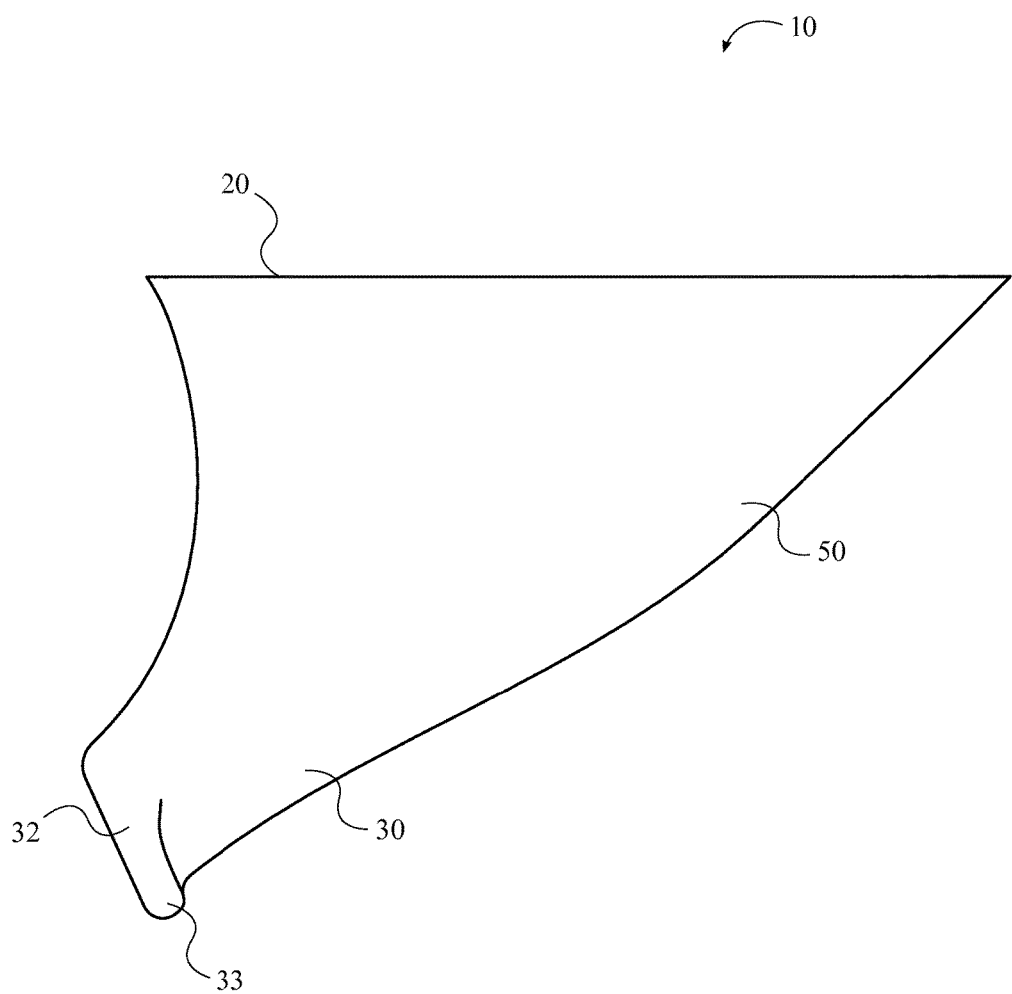
FIG. 3 is a right side elevational view of the present invention.

In reference to FIG. 2-3, the rim 20 is terminally positioned about the fluid collecting body 10 opposite the spout 30, wherein the rim 20 delineates a vulval opening 21 through which the user can urinate into the fluid collecting portion 60. The rim 20 is perimetrically connected to the concave interior surface 40 and the convex exterior surface 50, and is shaped to receive the bilateral symmetry of a female human crotch, as well as the anterior-to-dorsal asymmetry of a female human crotch. The rim 20 is ergonomically contoured in such a way as to prevent leaks when the present invention is held against the user's body. The rim 20 may also be ribbed in order to form a more reliable seal between the present invention and the user's body.

Figure 8:
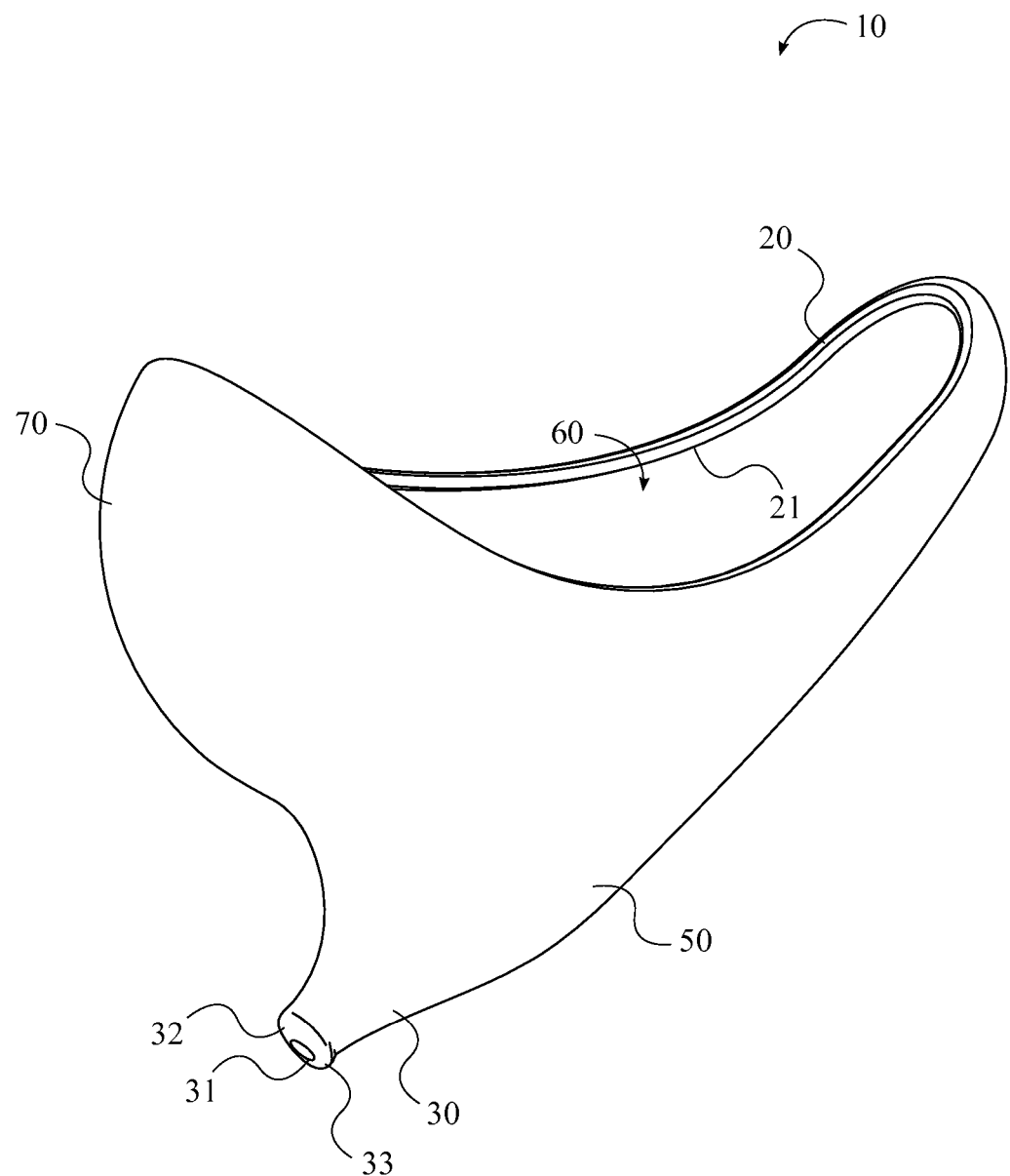
FIG. 8 is a perspective view of the present invention having a contoured lateral wall.
Figure 9:
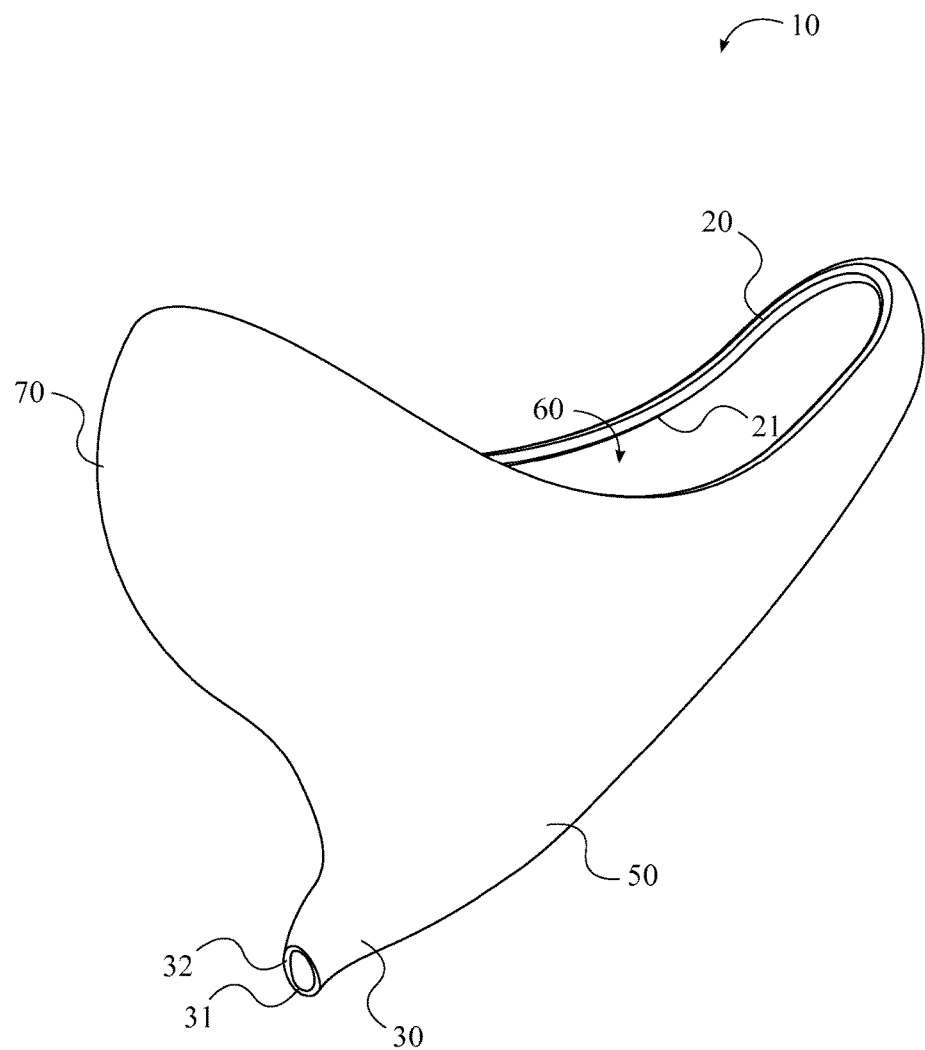
FIG. 9 is a perspective view of the present invention, wherein the spout is differently shaped, and wherein the urinary outflow opening is larger.
Figure 10:
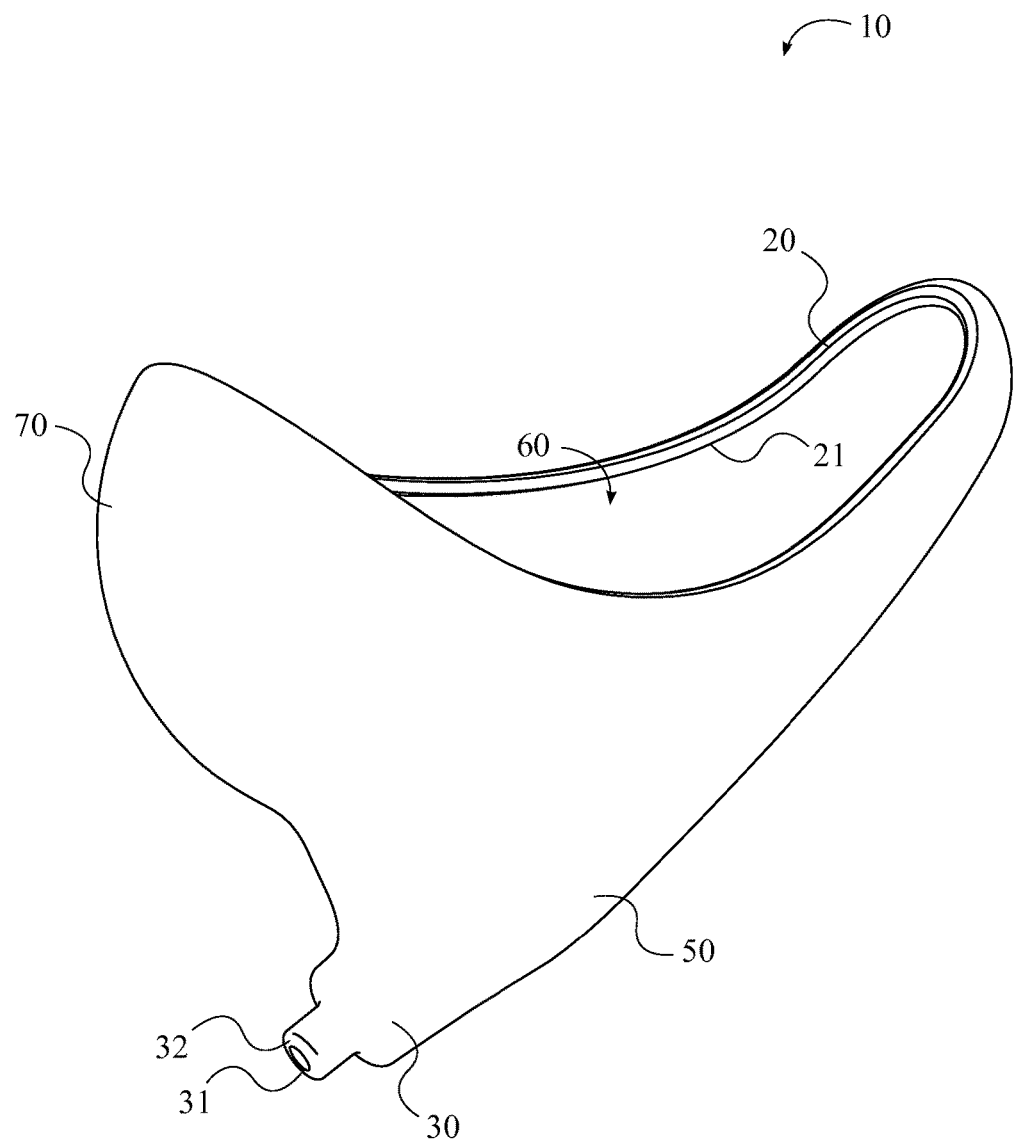
FIG. 10 is a perspective view of the present invention, wherein the spout comprises a primary extrusion and a secondary extrusion.

In reference to FIG. 8-10, in other embodiments of the present invention, the fluid collecting body 10 further comprises a contoured lateral wall 70. The contoured lateral wall 70 is perimetrically connected to the concave interior surface 40 and the convex exterior surface 50 opposite the spout 30. Furthermore, the rim 20 is perimetrically connected to the contoured lateral wall 70 opposite the concave interior surface 40 and the convex exterior surface 50, as opposed to being connected to the concave interior surface 40 and the convex exterior surface 50. Together, the contoured lateral wall 70 and the concave interior surface 40 delineate the fluid collecting portion 60, thus providing an enlarged interior volume. The contoured lateral wall 70 provides an enlarged circumference about which the rim 20 traverses compared to the concave interior surface 40 and the convex exterior surface 50 and thus the vulval opening 21 is larger. This allows the present invention to better conform to the user's body, allows the fluid collecting portion 60 to be more easily accessed and cleaned, and allows the user to better handle the present invention as the female urination device is used.

Figure 4:
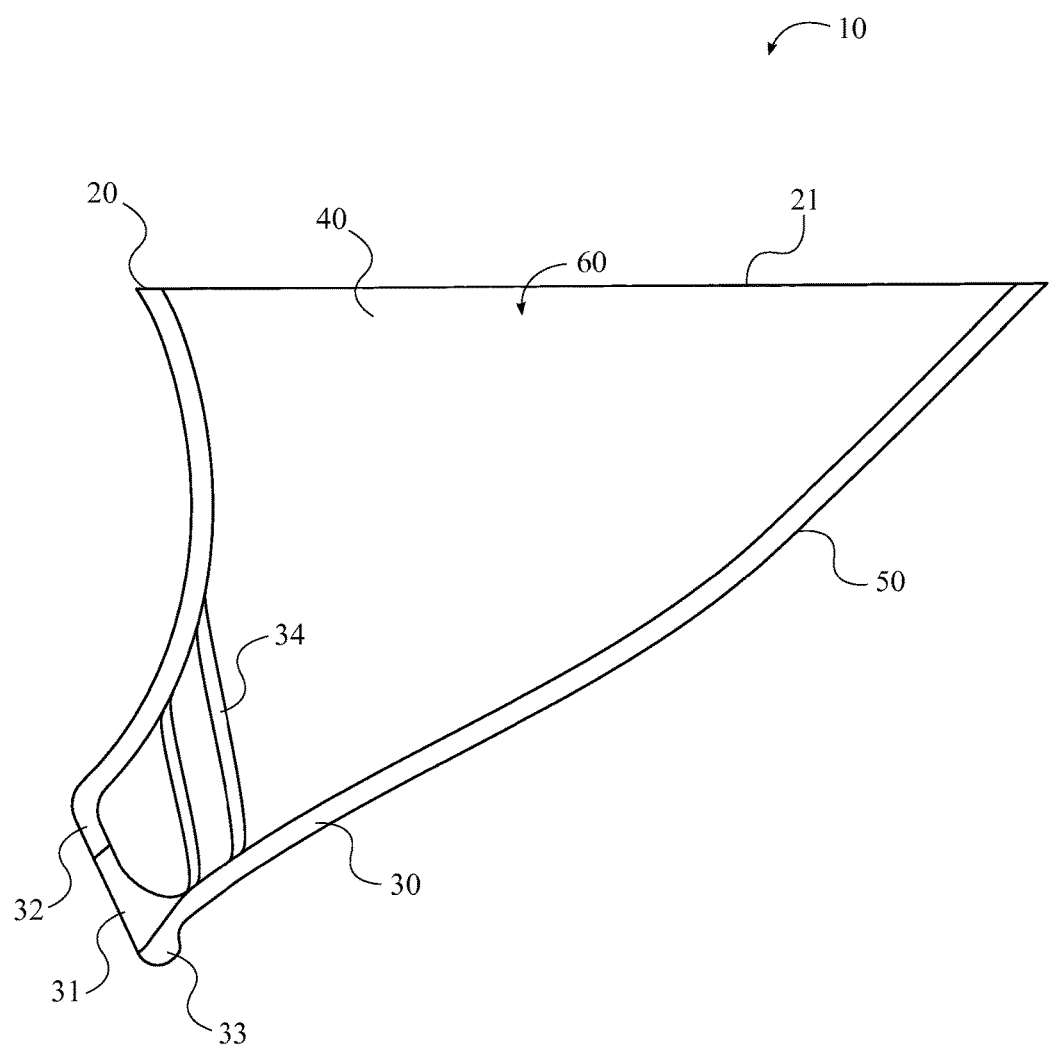
FIG. 4 is a right side sectional view, wherein a vortex groove is helically positioned along the spout.

The spout 30 is positioned about the fluid collecting body 10 opposite the rim 20 and provides the means through which urine, or menstrual outflow, exits the female urination device. As such, the spout 30 delineates a urinary outflow opening 31, wherein the urinary outflow opening 31 is smaller than the vulval opening 21 and is in fluid communication with the vulval opening 21 through the fluid collecting portion 60, as depicted in FIG. 4. The spout 30 is tapered away from the concave interior surface 40 and the convex exterior surface 50 in order to increase the flow rate of urine exiting the spout 30. In the preferred embodiment of the present invention, the spout 30 is tapered as a single extrusion of material. However, in other embodiments of the present invention the spout 30 may comprise a primary extrusion and a secondary extrusion; the secondary extrusion being adjacently connected to the primary extrusion opposite the concave interior surface 40 and the convex exterior surface 50, wherein the cross-sectional diameter of the secondary extrusion is smaller than the cross-sectional diameter of the primary extrusion, as depicted in FIG. 10.

In reference to FIG. 1, the spout 30 comprises a urinary lip 32, wherein the urinary lip 32 is terminally positioned on the spout 30 opposite the concave interior surface 40 and the convex exterior surface 50. As such, the urinary lip 32 delineates the urinary outflow opening 31. In the preferred embodiment of the present invention, the urinary lip 32 is ovular, being elongated away from the concave interior surface 40 and the convex exterior surface 50. Additionally, the urinary lip 32 comprises a lip protrusion 33, wherein the lip protrusion 33 is positioned about the urinary lip 32 opposite the concave interior surface 40 and the convex exterior surface 50, and extends away from the concave interior surface 40 and the convex exterior surface 50. The lip protrusion 33 extends out, away from the body of the spout 30. Together, the lip protrusion 33 and the ovular shape of the urinary lip 32 cause the urine to arc providing more control over the exiting flow of urine.

In the preferred embodiment of the present invention, the spout 30 is completely enclosed, however, in other embodiments of the present invention, the spout 30 may be open along the top forming a trough. The present invention is not limited with respect to the specific design of the spout 30 and the spout 30 design may vary according to various embodiments of the present invention. Further examples of differentiation in the spout 30 from one embodiment to another include the distance the spout 30 extends from the concave interior surface 40 and the convex exterior surface 50, and the angle of the spout 30 relative to the concave interior surface 40 and the convex exterior surface 50. In reference to FIG. 4, in one embodiment of the present invention, the spout 30 further comprises a vortex groove 34. The vortex groove 34 is positioned within the spout 30 and helically traverses along the spout 30. The vortex groove 34 induces a rotation in the urinary flow as the urine traverses down the spout 30 assisting in accelerating the outflow of urine.

Figure 5:
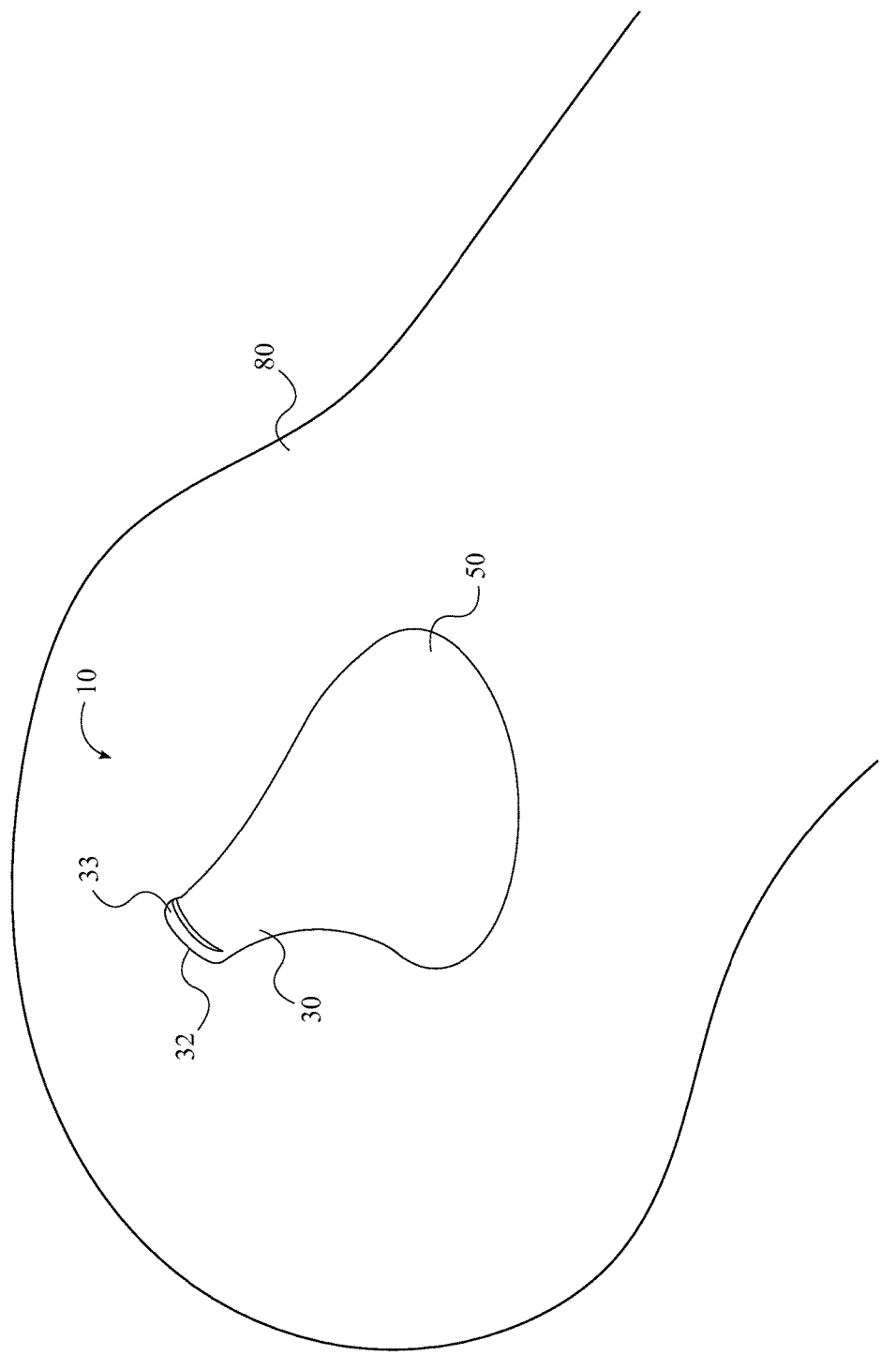
FIG. 5 is a bottom perspective view, wherein the fluid collecting body is either removably attached or permanently connected to a sanitary napkin.
Figure 6:
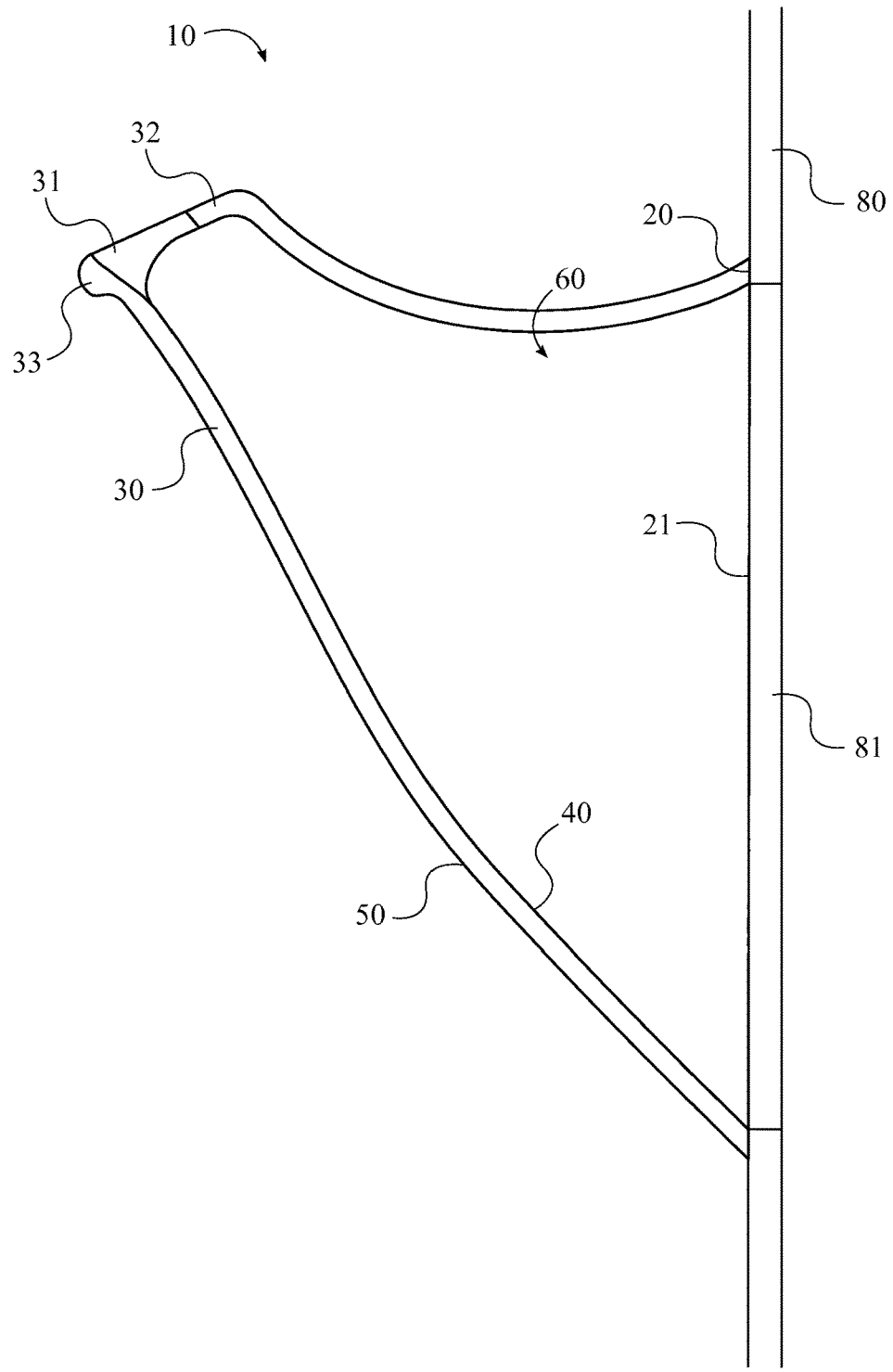
FIG. 6 is a right side sectional view, wherein the pad opening is aligned with the vulval opening.

The sanitary napkin 80 promotes good hygiene and assists in attaching the fluid collecting body 10 to the user's body. In reference to FIG. 5, the sanitary napkin 80 is either permanently fixed or removably attached to the rim 20 and comprises a pad opening 81 that is aligned with the vulval opening 21, as depicted in FIG. 6. In this way, the user can urinate through the pad opening 81 and into the fluid collecting portion 60 of the fluid collecting body 10. In reusable embodiments of the present invention, the sanitary napkin 80 is perimetrically attached to the rim 20, wherein the sanitary napkin 80 can be detached and disposed of after use, while the fluid collecting body 10 can be cleaned. In disposable embodiments of the present invention, the sanitary napkin 80 is perimetrically connected to the rim 20, wherein the sanitary napkin 80 and the fluid collecting body 10 are permanently connected and disposed of together. Preferably, both the sanitary napkin 80 and the fluid collecting body 10 are biodegradable in disposable embodiments of the present invention.

The sanitary napkin 80 also comprises a plurality of adhesive sections that allows the sanitary napkin 80 to be removably attached to the user's body. The plurality of adhesive sections is positioned perimetrically around the sanitary napkin 80, allowing each side of the sanitary napkin 80 to be adhered to the user's body. The plurality of adhesive sections assists in maintaining the leak proof seal between the rim 20 and the user's body and if any urine does manage to leak around the rim 20, the sanitary napkin 80 is able to absorb the urine.

The present invention provides women with a means of urinating in a standing position. To use the present invention, a user orients the fluid collecting body 10 such that the spout 30 is aligned with her labia majora, with the top front of the fluid collecting body 10 held firmly in place against the base of her mons veneris. The fluid collecting body 10 is held firmly in place to prevent leakage during use. The user then urinates through the vulval opening 21 into the fluid collecting portion 60 of the fluid collecting body 10 while holding the fluid collecting body 10 in place. Urine collects within the fluid collecting portion 60 of the fluid collecting body 10 and is directed out of the spout 30. The concave interior surface 40 assists in directing the flow of urine through the fluid collecting portion 60, towards the spout 30. As urine exits the fluid collecting body 10 through the spout 30, the urine is directed away from the user's hands, body, and clothes.

Figure 7:
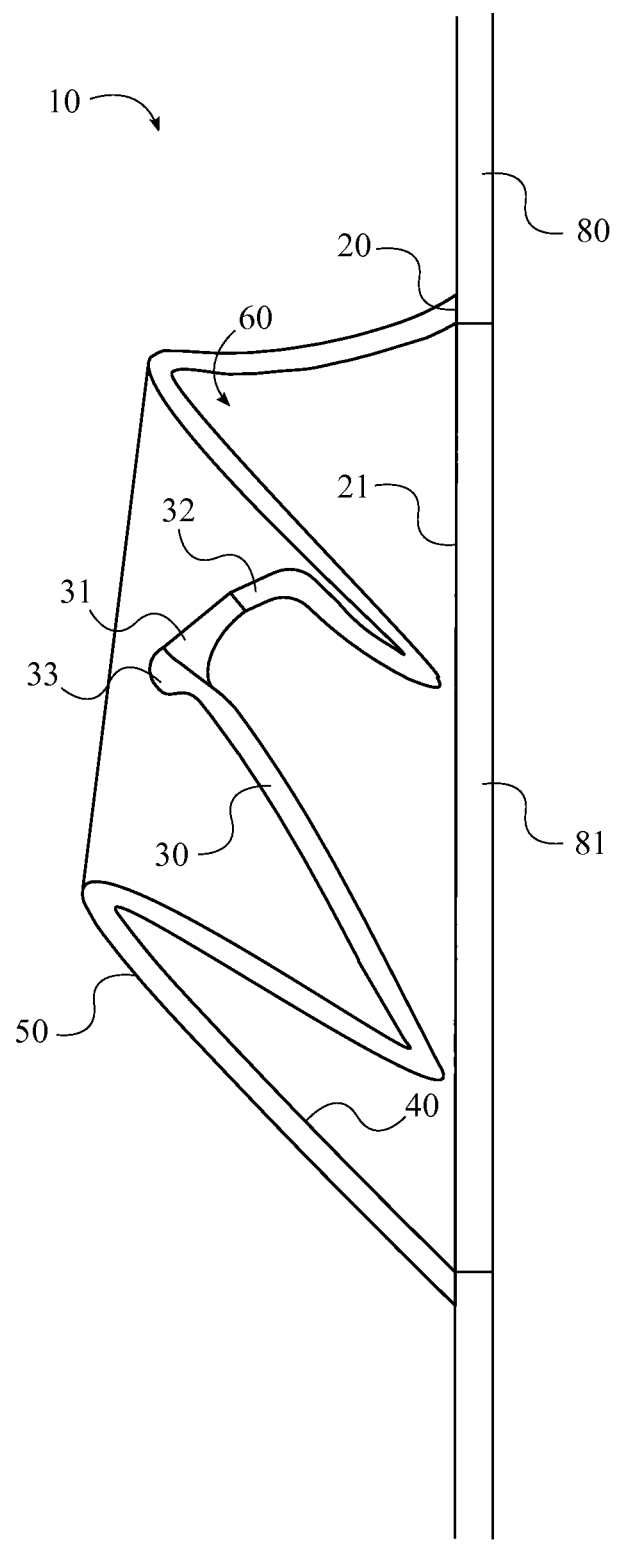
FIG. 7 is a right side sectional view, wherein the spout is positioned within the fluid collecting portion.

In some embodiments of the present invention, the fluid collecting body 10 is made from a flexible material, allowing the user to squeeze the fluid collecting body 10 as urine is collected. By squeezing the fluid collecting body 10, the user can increase the exiting flow rate of the urine by forcing urine from the fluid collecting portion 60 through the spout 30. The flexible nature of the fluid collecting body 10 is also beneficial in disposable embodiments of the present invention as it allows the fluid collecting body 10 to be folded in order to become more compact. For example, the spout 30 can be retracted into the fluid collecting portion 60, as depicted in FIG. 7, by pushing the spout 30 inwards, thus reducing the depth of the fluid collecting body 10. The sanitary napkin 80 can then be folded or rolled around the fluid collecting body 10 to maintain the position of the spout 30 and the low profile of the fluid collecting body 10. The spout 30 can then be easily extended by unfolding the sanitary napkin 80 and pushing the spout 30 outwards.

The present invention is intended for use in situations in which urinating in a sitting position is unsanitary, uncomfortable, or inconvenient. An example situation encompasses public restrooms that are shared and used by a large number of people on a daily basis. The present invention allows a woman to avoid sitting on a potentially unsanitary toilet seat in favor of urinating from a standing position. Additionally, the present invention allows women to utilize unisex toilets as well as male urinals. The present invention is a practical solution for situations in which there is no direct access to a restroom, such as in the outdoors.

In a reusable configuration, the present invention is washable after every use. In the reusable configuration, the fluid collecting body 10 is constructed from a material such as hypoallergenic silicon for convenient washing after use. In a disposable configuration of the present invention, the fluid collecting body 10 is constructed from paper or a biodegradable and hypoallergenic material such as cellulose bamboo pulp fiber to minimize potential negative effects on the environment after disposal.

Although the invention has been explained in relation to its preferred embodiment, it is to be understood that many other possible modifications and variations can be made without departing from the spirit and scope of the invention as hereinafter claimed.

What is claimed is:

1. A female urination device comprising:
   a fluid collecting body;
   the fluid collecting body comprising a rim, a spout, a concave interior surface and a convex exterior surface;
   the spout being perimetrically connected to the concave interior surface and the convex exterior surface;
   the concave interior surface and the convex exterior surface being positioned in between the rim and the spout;
   the concave interior surface and the convex exterior surface being tapered from the rim to the spout;
   the concave interior surface delineating a fluid collecting portion;
   the rim delineating a vulval opening;
   the spout delineating a urinary outflow opening;
   the urinary outflow opening being smaller than the vulval opening;
   the urinary outflow opening being in fluid communication with the vulval opening via the fluid collecting portion so as to form a trough in between the vulval opening and the urinary outflow opening;
   the spout comprising a primary extrusion and a secondary extrusion;
   the secondary extrusion being adjacently connected to the primary extrusion opposite the concave interior surface and the convex exterior surface;
   a cross-sectional diameter of the secondary extrusion being smaller than a cross-sectional diameter of the primary extrusion so as to form a ladder step in between the primary extrusion and the secondary extrusion;
   the spout being retractable into the fluid collecting portion; and
   the spout being entirely accommodated within the fluid collecting portion in response to the spout being retracted into the fluid collecting portion.

2. The female urination device as claimed in claim 1 comprising:
   a sanitary napkin;
   the sanitary napkin comprising a pad opening;
   the sanitary napkin being perimetrically attached to the rim; and
   the pad opening being aligned with the vulval opening.

3. The female urination device as claimed in claim 1 comprising:
   a sanitary napkin;
   the sanitary napkin comprising a pad opening;
   the sanitary napkin being perimetrically connected to the rim; and
   the pad opening being aligned with the vulval opening.

4. The female urination device as claimed in claim 1 comprising:
   the rim being perimetrically connected to the concave interior surface and the convex exterior surface.

5. The female urination device as claimed in claim 1 comprising:
   the fluid collecting body comprising a contoured lateral wall;
   the contoured lateral wall being perimetrically connected to the concave interior surface and the convex exterior surface opposite the spout; and
   the rim being perimetrically connected to the contoured lateral wall opposite the concave interior surface and the convex exterior surface.

6. The female urination device as claimed in claim 1, wherein the rim is shaped to receive the bilateral symmetry of a female human crotch.

7. The female urination device as claimed in claim 1, wherein the rim is shaped to receive the anterior-to-dorsal asymmetry of a female human crotch.

8. The female urination device as claimed in claim 1, wherein the fluid collecting body is flexible such that the spout is retractable into the fluid collecting portion.

9. The female urination device as claimed in claim 1, wherein the rim is ribbed.

10. The female urination device as claimed in claim 1, wherein the spout is tapered away from the concave interior surface and the convex exterior surface.

11. The female urination device as claimed in claim 1 comprising:
the spout comprising a vortex groove;
the vortex groove being positioned within the spout; and
the vortex groove helically traversing along the spout.

12. The female urination device as claimed in claim 1, wherein the fluid collecting body is biodegradable.

13. The female urination device as claimed in claim 1 comprising:
the spout comprising a urinary lip;
the urinary lip being terminally positioned on the spout opposite the concave interior surface and the convex exterior surface; and
the urinary lip delineating the urinary outflow opening.

14. The female urination device as claimed in claim 13, wherein the urinary lip is ovular.

15. The female urination device as claimed in claim 13 comprising:
the urinary lip comprising a lip protrusion;
the lip protrusion being positioned about the urinary lip opposite the concave interior surface and the convex exterior surface; and
the lip protrusion extending away from the concave interior surface and the convex exterior surface.

16. A female urination device comprising:
a fluid collecting body;
the fluid collecting body comprising a rim, a spout, a concave interior surface, a convex exterior surface and a contoured lateral wall;
the spout comprising a urinary lip;
the urinary lip comprising a lip protrusion;
the spout being perimetrically connected to the concave interior surface and the convex exterior surface;
the concave interior surface and the convex exterior surface being positioned in between the rim and the spout;
the concave interior surface and the convex exterior surface being tapered from the rim to the spout;
the concave interior surface delineating a fluid collecting portion;
the contoured lateral wall being perimetrically connected to the concave interior surface and the convex exterior surface opposite the spout;
the rim being perimetrically connected to the contoured lateral wall opposite the concave interior surface and the convex exterior surface;
the rim delineating a vulval opening;
the urinary lip being terminally positioned on the spout opposite the concave interior surface and the convex exterior surface;
the lip protrusion being positioned about the urinary lip opposite the concave interior surface and the convex exterior surface;
the lip protrusion extending away from the concave interior surface and the convex exterior surface;
the urinary lip delineating a urinary outflow opening;
the urinary outflow opening being smaller than the vulval opening;
the urinary outflow opening being in fluid communication with the vulval opening via the fluid collecting portion so as to form a trough in between the vulval opening and the urinary outflow opening;
the rim being shaped to receive the bilateral symmetry of a female human crotch;
the rim being shaped to receive the anterior-to-dorsal asymmetry of a female human crotch;
the spout comprising a primary extrusion and a secondary extrusion;
the secondary extrusion being adjacently connected to the primary extrusion opposite the concave interior surface and the convex exterior surface;
a cross-sectional diameter of the secondary extrusion being smaller than a cross-sectional diameter of the primary extrusion so as to form a ladder step in between the primary extrusion and the secondary extrusion;
the spout being retractable into the fluid collecting portion; and
the spout being entirely accommodated within the fluid collecting portion in response to the spout being retracted into the fluid collecting portion.

17. The female urination device as claimed in claim 16 comprising:
a sanitary napkin;
the sanitary napkin comprising a pad opening;
the sanitary napkin being perimetrically attached to the rim; and
the pad opening being aligned with the vulval opening.

18. The female urination device as claimed in claim 16, wherein the rim is ribbed.

19. The female urination device as claimed in claim 16, wherein the spout is tapered away from the concave interior surface and the convex exterior surface.

20. The female urination device as claimed in claim 16 comprising:
the spout comprising a vortex groove;
the vortex groove being positioned within the spout; and
the vortex groove helically traversing along the spout.

* * * * *